(12) United States Patent
Jang et al.

(10) Patent No.: US 11,786,943 B2
(45) Date of Patent: Oct. 17, 2023

(54) DOCKING APPARATUS FOR MOBILE ROBOT

(71) Applicant: LG ELECTRONICS INC., Seoul (KR)

(72) Inventors: Jaewon Jang, Seoul (KR); Youngbin Kim, Seoul (KR); Yeongjae Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 449 days.

(21) Appl. No.: 16/944,227

(22) Filed: Jul. 31, 2020

(65) Prior Publication Data

US 2021/0031244 A1   Feb. 4, 2021

(30) Foreign Application Priority Data

Jul. 31, 2019   (KR) .......................... 10-2019-0093486
Dec. 27, 2019   (KR) .......................... 10-2019-0176629

(51) Int. Cl.
| | | |
|---|---|---|
| *B08B 7/00* | (2006.01) | |
| *A47L 11/24* | (2006.01) | |
| *A47L 11/282* | (2006.01) | |
| *A47L 11/40* | (2006.01) | |
| *A61L 2/10* | (2006.01) | |
| *A61L 2/26* | (2006.01) | |

(52) U.S. Cl.
CPC ............ *B08B 7/0057* (2013.01); *A47L 11/24* (2013.01); *A47L 11/282* (2013.01); *A47L 11/4038* (2013.01); *A47L 11/4091* (2013.01); *A61L 2/10* (2013.01); *A61L 2/26* (2013.01); *A47L 2201/028* (2013.01); *A61L 2202/11* (2013.01)

(58) Field of Classification Search
CPC ...... B08B 7/0057; A47L 11/24; A47L 11/282; A47L 11/4038; A47L 11/2091; A61L 2/10; A61L 2/26; A61L 2202/11
See application file for complete search history.

(56) References Cited

FOREIGN PATENT DOCUMENTS

| | | |
|---|---|---|
| KR | 10-2006-0027207 | 3/2006 |
| KR | 10-2013-0088253 | 8/2013 |
| KR | 10-2015-0006525 | 1/2015 |
| KR | 10-2015-0073592 | 7/2015 |
| KR | 10-2015-0073735 | 7/2015 |
| KR | 10-0729397 | 6/2017 |

(Continued)

OTHER PUBLICATIONS

Translation for KR1020060027207 (Year: 2006).*

(Continued)

*Primary Examiner* — Sean E Conley
(74) *Attorney, Agent, or Firm* — Birch, Stewart, Kolasch & Birch, LLP

(57) ABSTRACT

The present disclosure relates to a docking apparatus for a mobile robot including a sterilization unit, which emits germicidal light to a floor cloth to sterilize the floor cloth, and which includes: a germicidal lamp which vertically overlaps with the floor cloth of the mobile robot, and emits the germicidal light to a front end thereof; a diffusing part for diffusing the germicidal light to a rear end of the germicidal lamp; and a converging part for converging the germicidal light to a rear end of the diffusing part.

16 Claims, 9 Drawing Sheets

(56) References Cited

FOREIGN PATENT DOCUMENTS

TW 201907850 A 3/2019

OTHER PUBLICATIONS

Translation for KR1020150073735 (Year: 2015).*
European Search Report, dated Dec. 9, 2020, issued in European Patent Application No. 20188611.6 (6 pages).
PCT Search Report, dated May 27, 2020, issued in PCT International Patent Application No. PCT/KR2020/001344 (3 pages).
Office Action, dated Oct. 26, 2021, issued in Taiwanese Patent Application No. 109125645 (4 pages).

* cited by examiner

DOCKING APPARATUS FOR MOBILE ROBOT

TECHNICAL FIELD

The following description relates to a docking apparatus for a mobile robot, and more particularly to a docking apparatus for a mobile robot, which emits germicidal light to the mobile robot when the mobile robot is docked.

BACKGROUND

Robots have been developed for industrial use and have been part of factory automation. Recently, the application filed of robots has been expanded, such that medical robots, aerospace robots, and the like have been developed and household robots that can be used in ordinary homes have also been manufactured. Among these robots, a robot that can travel by itself is called a mobile robot.

A typical example of the mobile robot used in home is a robot cleaner. The robot cleaner is a home appliance which cleans a certain area by sucking dust or foreign materials from the floor while moving autonomously in the area.

Such robot cleaner is generally composed of a cleaning robot and a docking apparatus. The cleaning robot is provided with a rechargeable battery, and may move freely and autonomously using operating power of the battery. The cleaning robot performs cleaning by wiping foreign matter from the floor with a floor cloth, and if necessary, returns to the docking apparatus to charge the battery.

Related art 1 discloses: a charging apparatus which is provided with a power source and an electrically connected terminal; and a mobile robot which includes a corresponding terminal to be electrically connected to the terminal of the charging apparatus. Once the terminal of the charging apparatus and the terminal of the mobile robot come into contact with each other, charging of the mobile robot is started.

The mobile robot may be electrically connected to the terminal of the charging apparatus only when the mobile robot moves to the charging apparatus and is docked in a correct position. However, the related art has a problem in that a means for guiding the mobile robot to be mounted in a correct docking area by traveling autonomously.

Related art 2 discloses a mobile robot which is moved by a floor cloth surface. In the related art, the mobile robot includes a first rotating member and a second rotating member, which are disposed with respect to a vertical axis, and fix a pair of floor cloth surfaces disposed in a left-right direction. The mobile robot in the related art moves by the rotation of the first rotating member and the second rotating member, when only the floor cloth surfaces, which are fixed to the first rotating member and the second rotating member, are in contact with the floor.

Particularly, in the related art 1, the bottom surface of the charging apparatus is inclined, such that when the general robot cleaner moves forward with a driving force, the body of the robot cleaner is lifted up, thereby allowing a charging terminal of the mobile robot and a corresponding terminal of the charging apparatus to come into contact with each other. However, in a mobile robot which moves by a frictional force between a spin mop and the floor, there is a problem in that a driving force of the mobile robot is too weak to climb a slope to lift up the body, and has no means for finely and accurately adjusting a traveling direction of the mobile robot.

The related art also has a problem in that there is no means for sterilizing a floor cloth provided for mobile robot while the mobile robot is docked for charging.

SUMMARY

In the case of a mobile robot, which moves by a frictional force between a spin mop and a floor without wheels, the mobile robot may not climb a docking apparatus if a base of the docking apparatus is too thick. Accordingly, it is an object of the present disclosure to provide a docking apparatus for a mobile robot, in which the mobile robot may easily climb the docking apparatus, a germicidal lamp and reflecting plates are disposed in a thin base, and has a wide radiation angle.

In order to emit germicidal light to the entire spin mop while having a base, it is required to install a light source over the base. It is another object of the present disclosure to provide a docking apparatus for the mobile robot, in which: a number of germicidal lamps may be reduced; light of the germicidal lamp may be provided to a region, which extends from the center of the spin mop to an outer circumference, by using reflecting plates; and by rotating the spin mop, the entire spin mop may be sterilized effectively with a reduced number of germicidal lamps.

It is yet another object of the present disclosure to provide a docking apparatus for a mobile robot, in which light in a lateral direction may be converted to light in an upward direction, thereby uniformly emitting germicidal light over a wide area.

It is still another object of the present disclosure to provide a docking apparatus for a mobile robot, in which germicidal light does not leak to the outside of a floor cloth.

The objects of the present disclosure are not limited to the aforementioned objects and other objects not described herein will be clearly understood by those skilled in the art from the following description.

In order to achieve the above objects, a docking apparatus for a mobile robot according to an embodiment of the present disclosure includes: a plate connected to a lower end of a main body, and having a space for docking the mobile robot; and a sterilization unit disposed inside the plate, and configured to emit germicidal light to a floor cloth disposed at a lower portion of the mobile robot.

The sterilization unit may be disposed below an upper end of the plate; a germicidal lamp is disposed at a front end of the sterilization unit; a lower reflecting plate is disposed at a lower end of the germicidal lamp; side reflecting plates are inclined upward from both side surfaces of the lower reflecting plate.

Specifically, in accordance with an aspect of the present disclosure, the above and other objects can be accomplished by providing a docking apparatus for a mobile robot, the docking apparatus including: a main body having a power module; a plate connected to a lower end of the main body, and having a space for docking the mobile robot; and a sterilization unit disposed inside the plate, and configured to emit germicidal light to an upper portion of the plate, wherein the sterilization unit may include: a germicidal lamp for emitting germicidal light; and a reflection module configured to reflect the light, emitted from the germicidal lamp, to the upper portion of the plate.

The reflection module may include: a light-provided surface, to which the light of the germicidal lamp is provided; and reflecting plates, which are connected to the light-provided surface, have a wider area than the light-provided surface and a surface intersecting the light-provided surface, and reflect the light of the germicidal lamp.

The reflecting plates may include: a diffusing part, one end of which is connected to the light-provided surface, and has a width which increases further away from the light-provided surface; and a converging part, one end of which is connected to the diffusing part, and has a width which decreases further away from the light-provided surface.

The reflecting plates may include: a lower reflecting plate, which has a surface parallel to an upper surface of the plate, and is disposed below the germicidal lamp; and side reflecting plates which are connected to at least both ends of the lower reflecting plate, and have a slope which is inclined upward further away from the lower reflecting plate.

The reflection module may further include a blocking plate which covers an upper portion of the diffusing part.

The sterilization unit may be disposed below an upper end of the plate, and may emit the germicidal light upward.

A width of the side reflecting plates may increase further away from the light-provided surface, and then may be reduced.

A width of the lower reflecting plate may increase further away from the light-provided surface, and then may be reduced.

The side reflecting plates may include: a rear reflecting plate, which is disposed to face the light-provided surface and is connected to one end of the lower reflecting plate; and a left reflecting plate and a right reflecting plate, which are disposed to face each other and are connected to the lower reflecting plate and the rear reflecting plate.

When viewed from the top, an angle formed between the left reflecting plate and the right reflecting plate may be an acute angle.

The blocking plate may be disposed on an upper portion of the germicidal lamp, and may block the germicidal light.

The blocking plate may be spaced apart upward from the reflecting plates, and may vertically overlap with the diffusing part.

The converging part may vertically overlap with a floor cloth, while the diffusing part may not vertically overlap with the floor cloth.

A longitudinal length of the converging part may be equal to or greater than a length of a radius of a circular floor cloth.

The germicidal lamp may emit the germicidal light obliquely to the lower reflecting plate.

The germicidal lamp may emit UVC rays.

A length of the converging part may be greater than a length of the diffusing part.

In accordance with another aspect of the present disclosure, the above and other objects can be accomplished by providing a method of controlling a mobile robot system, the method including: detecting whether a mobile robot is docked to a docking apparatus; when the mobile robot is docked to the docking apparatus, turning on a germicidal lamp of the docking apparatus; and while the germicidal lamp is on, rotating a spin mop of the mobile robot in one direction.

In the rotating of the spin mop, the spin mop may make at least one rotation.

In the rotating of the spin mop, the spin mop may rotate by a preset angle at every preset time.

Details of other embodiments are included in the detailed description and the accompanying drawings.

According to the present disclosure, the docking apparatus for the mobile robot has one or more of the following effects.

Firstly, when viewed from the top, an angle formed between the left reflecting plate and the right reflecting plate may be an acute angle, such that a radiation region of germicidal light has a triangular shape or a fan shape, thereby allowing the germicidal light to be emitted uniformly.

Secondly, when viewed from the top, the sterilization unit has the diffusing part, in which the germicidal light is diffused, and the converging part, in which the diffused germicidal light converges, thereby allowing the germicidal light to be emitted uniformly.

Thirdly, the blocking plate may be disposed in a region, in which the floor mop and the reflecting plates do not overlap each other, such that leaking germicidal light may be blocked.

However, the effects of the present disclosure are not limited to the aforesaid, and other effects not described herein will be clearly understood by those skilled in the art from the following description of the appended claims.

DETAILED DESCRIPTION

Figure 1:
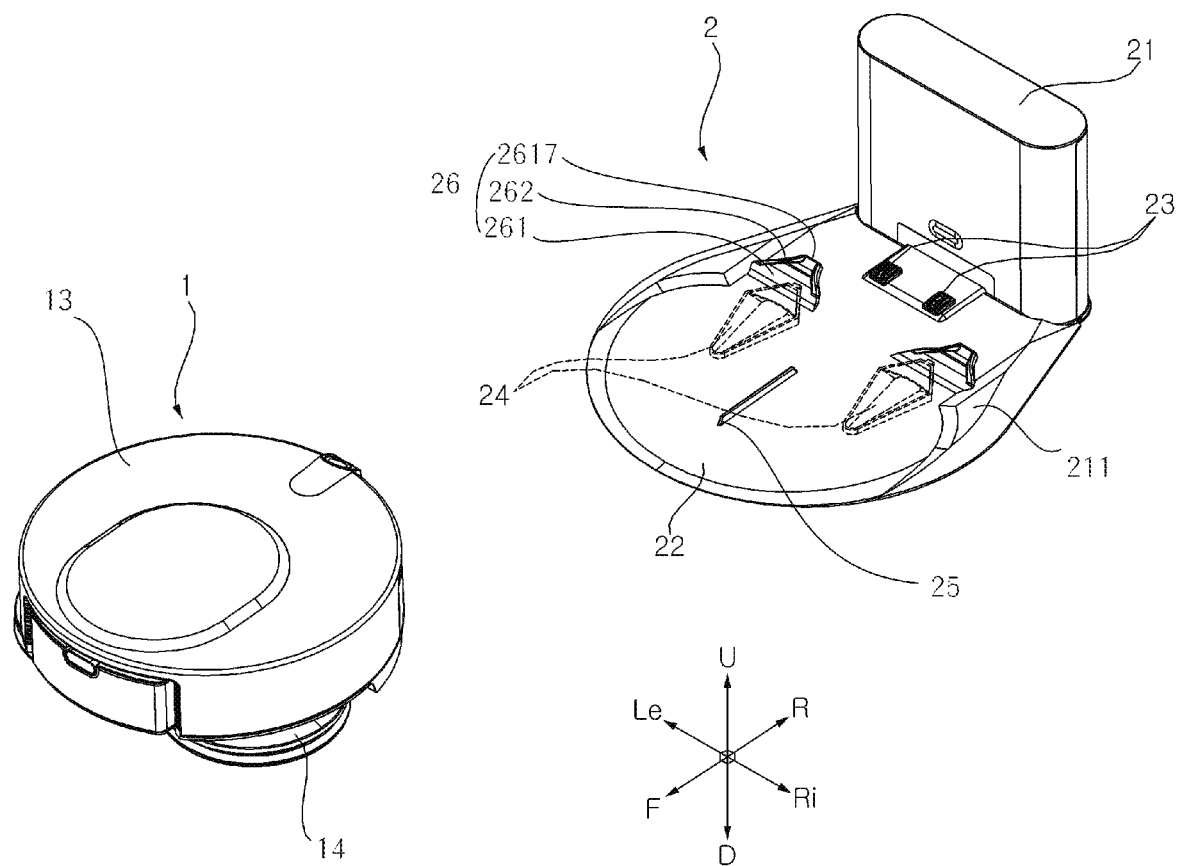
FIG. 1 is a perspective view of a robot cleaner and a docking apparatus according to an embodiment of the present disclosure.

Advantages and features of the present disclosure and methods for accomplishing the same will be more clearly understood from exemplary embodiments described below with reference to the accompanying drawings. However, the present disclosure is not limited to the following embodiments, but may be implemented in various different forms. The embodiments are provided only to complete disclosure of the present disclosure and to fully provide a person having ordinary skill in the art, to which the present disclosure pertains, with the category of the present disclosure, and the present disclosure will be defined by the scope of the appended claims. Wherever possible, like reference numerals generally denote like elements through the specification.

In the following description, the terms indicating directions, such as "front (F)," "rear (R)," "left (Le)," "right (RI)," "up (U)," "down (D)," and the like, are defined based on a traveling direction of a mobile robot. A direction, in which the mobile robot is docked on a charging apparatus 2, is defined as a front direction, and a direction opposite to the front direction is defined as a rear direction. A direction of the left side/right side of the charging apparatus 2 may be determined based on a position when the charging apparatus 2 is viewed from above. These terms, however, are used merely to provide a better understanding of the present disclosure, and it is apparent that the directions can be defined differently by difference references.

A vertical central axis Ay refers to a virtual line which extends in a font-rear direction from the center of the docking apparatus 2. A horizontal central axis Ax refers to a horizontal line formed by connecting centers of both spin mops when the mobile robot 1 docked.

An object to be sterilized is an element which is sterilized by germicidal light, and may be any object such as floor cloth, rag, and the like. The term "floor cloth" used herein may be made of various materials, such as fabric or paper, and may be intended for repetitive use by washing or for one-time use.

The present disclosure may be applied to a mobile robot which may be manually moved by a user, a robot cleaner which may move autonomously, and the like. The following description will be given using a mobile robot 1 as an example.

The terms, "first," "second," "third," etc., used in this disclosure, do not necessarily denote any order, importance, or hierarchy, but rather the terms are used to merely distinguish one element from another. For example, an embodiment may be configured to include only a second element without a first element.

A mobile robot 1 according to an embodiment of the present disclosure includes a body 13 including a controller. The mobile robot 1 includes a mop module 14 configured to mop a floor while being in contact with the floor (surface to be cleaned). The mobile robot 1 includes a sweep module (not shown) configured to collect foreign materials from the floor.

The mop module 14 is disposed on a lower side of the body 13 and supports the body 13. The sweep module is disposed on a lower side of the body 13 and supports the body 13. In the embodiment, the body 13 is supported by the mop module 14 and the sweep module. The body 13 forms an exterior of the mobile robot 1. The body 13 is disposed to connect the mop module 14 and the sweep module.

The mop module 14 may form an exterior. The mop module 14 is disposed on a lower side of the body 13 and at the rear of the sweep module. The mop module 14 provides a driving force for movement of the mobile robot 1. In order to move the mobile robot 1, the mop module 14 is preferably disposed at the rear of the mobile robot 1.

The mop module 14 includes at least one floor cloth 143 which wipes the floor while rotating. The mop module 14 includes at least one spin mop 141, which when viewed from above, rotates clockwise or counter-clockwise. The spin mop 141 is in contact with the floor.

In the embodiment, the mop module 14 includes a pair of spin mops 141a and 141b. The pair of spin mops 141a and 141b rotate clockwise or counter-clockwise when viewed from above, and mops the floor while rotating. Of the pair of the spin mops 141a and 141b, a spin mop, which is located at the left side when viewed from the front in a traveling direction of the mobile robot 1, is defined as a left spin mop 141a, and a spin mop located at the right side is defined as a right spin mop 141b.

Each of the left spin mop 141a and the right spin mop 141b rotates about its own rotational axis. The rotational axis is disposed vertically. The left spin mop 141a and the right spin mop 141b may rotate independently of each other.

Each of the left spin mop 141a and the right spin mop 141b includes the floor cloth 143, a rotary plate (not shown) and a spin shaft (not shown). Each of the left spin mop 141a and the right spin mop 141b includes a water accommodating part (not shown).

The sweep module (not shown) may form an exterior. The sweep module is disposed at the front of the mop module 14. In order to prevent the mop module 14 from first coming into contact with foreign materials on the floor, the sweep module is preferably disposed at the front in a traveling direction of the mobile robot 1.

The sweep module (not shown) is spaced apart from the mop module 14. The sweep module is disposed at the front of the mop module 14 and is in contact with the floor. The sweep module collects foreign materials from the floor.

While being in contact with the floor, the sweep module collects foreign materials, located in front of the sweep module, into the inside while the mobile robot 1 moves. The sweep module is disposed on a lower side of the body 13. The sweep module has a horizontal width which is smaller than a horizontal width of the mop module 13.

A caster (not shown) is disclosed on a lower side of the mobile robot 1, and partially supports the load of the mobile robot 1. The caster may be disposed at the front of the mobile robot 1. The caster may be disposed on both front sides of the mobile robot 1. The caster may be disposed forward of the mop module 14. The caster may be disposed forward of the sweep module. The caster has wheels to move the mobile robot 1.

A docking unit 2 may include a main body 21 including a power module, and a plate 22 coupled to a lower end of the main body 21. The mobile robot 1 may be docked on the plate 22.

The plate 22 includes the caster guide 26 to guide the caster provided at the front lower end of the mobile robot 1. The plate 22 guides the mobile robot 1 to a docking area through the caster guide 26, and guides a charging terminal 23 and a corresponding terminal 23' to come into contact with each other while vertically overlapping each other.

The plate 22 guides the mobile robot 1 to a docking area, and guides the charging terminal 23 and the corresponding terminal 23' to come into contact with each other while vertically overlapping each other.

The main body 21 of the docking unit 2 may be connected to a front end of the plate 22 and may protrude upward to form a wall. In this case, the main body 21 may function as a separation prevention wall, which prevents separation of the mobile robot 1 when the mobile robot 1 moves forward away from a proper docking area on the plate 22.

The main body 21 may include a power module. The power module is electrically connected to an external power source, to be supplied with external electricity. The power module is electrically connected to the charging terminal 23, to supply the received electricity to the charging terminal 23.

The plate 22 may have a circular shape. The plate 22 may have a similar shape as the shape of the mobile robot 1. However, the shape of the plate 22 is not limited thereto, and may include simple changes to a polygonal shape and the like, which may be made by those skilled in the art.

The mobile robot 1 is docked to an upper end of the plate 22. Referring to FIG. 1, the mobile robot 1 is docked to a circular flat surface, which is referred to as a docking area.

The plate 22 may include a slope formed at the rear thereof. The mobile robot 1 may move toward the docking area by climbing the slope. The slope may be formed around a circumference of a rear edge of the plate 22.

The plate 22 may include a protruding part 221 which protrudes upward from a side surface or a front surface. The protruding part 221 may be formed at the end of the slope formed at the rear of the plate 22. The protruding part 221 may be formed on a circumference of the docking area. The slope may be formed around a rear circumference of the docking area, and the protruding part 221 may be formed at the end of the slope. The protruding part 221 may prevent the mobile robot 1 from separating from the docking area, and may guide the caster to the caster guide 24.

The protruding part 221 may have a wide rear portion and a narrow front portion. The protruding part 221 may be formed from a side surface to the front surface along the circumference of the circular plate 22. Accordingly, when the mobile robot 1 enters while moving away from the docking area, it is possible to guide the caster to the caster guide 26 which is positioned at an inner front portion.

The charging terminal 23 is a device which is electrically connected to the mobile robot 1 to charge a battery provided in the mobile robot 1. The charging terminal 23 protrudes from a front upper portion of the plate 22 of the charging apparatus 2, and is electrically connected to the power module of the docking unit 2. The charging terminal 23 may be disposed at the front of the plate 22. A pair of left and right charging terminals 23 may be disposed to be symmetrical to each other with respect to a vertical central axis.

The mobile robot 1 includes a corresponding terminal 23', which corresponds to the charging terminal 23 of the docking unit 2. The corresponding terminal 23' of the mobile robot 1 may protrude downward, so as to be electrically connected to the charging terminal 23 of the docking unit 2. The charging terminal 23' of the mobile robot 1 may be disposed at the front of the mobile robot 1.

The caster guide 26 may include: a guide surface 261, on which the caster, being in contact with the guide surface 261, moves by rolling; a separation prevention wall 262 which is disposed on a side surface of the guide surface 261; and a stopper 2617 which is disposed at the front of the guide surface 261. A pair of left and right caster guides 24 may be formed with respect to the vertical central axis.

The caster guide 26 may include the separation prevention wall 262, which is disposed on a side surface of the guide surface 261, and which protrudes upward. The separation prevention wall 262 may function to prevent the caster, moving on the guide surface 261, from being separated from the guide surface 261.

The stopper 2617 is disposed at the front of the caster guide 26 to prevent the caster from being separated by passing the caster guide 26. The stopper 2617 is connected to the front end of the guide surface 261 and protrudes upward.

Referring to FIG. 1, when the caster guide 26 is viewed from the top, a width of a front portion of the caster guide 26 is narrower than a width of a rear end thereof. When viewed from the top, the caster guide 26 may have a narrow front portion and a wide rear portion.

A guide pin 25 is disposed at an upper center portion of the plate 22, and is inserted between two spin mops to guide the mobile robot 1.

The guide pin 25 is disposed at the upper center portion of the plate 22. The guide pin 25 may be disposed in the docking area. The guide pin 25 protrudes upward. The guide pin 25 may be integrally formed with the plate 22, or may be formed separately and connected to the plate 22.

The guide pin 25 may extend from the upper center portion of the plate 22 along the vertical central axis. Two spin mops or a rotary plate may be adjacent to both side surfaces of the guide pin 25.

A sterilization unit 24 will be described below with reference to FIGS. 1 to 4.

The sterilization unit 24 emits germicidal light onto the floor cloth to sterilize the cloth. The sterilization unit 24 is disposed inside the plate 22 of the docking unit 2. As the sterilization unit 24 is provided inside the plate 22, a thickness of the plate 22 may be reduced, thereby allowing the mobile robot 1 to easily climb the plate 22.

The sterilization unit 24 emits germicidal light to an upper portion of the plate 22. The floor cloth of the mobile robot 1 is positioned on a portion of the top of the sterilization unit 24. The sterilization unit 24 emits germicidal light onto the floor cloth, positioned on the top thereof, to sterilize or disinfect the cloth. The sterilization unit 24, which is provided with a germicidal lamp for radiating germicidal light, may emit germicidal light. The sterilization unit 24 has reflecting plates formed at lower and side portions, to emit germicidal light, radiated from the lamp, onto the floor cloth positioned at the top.

The sterilization unit 24 is disposed in the plate 22. The sterilization unit 24 is disposed below an upper surface of the plate 22. When the mobile robot 1 is docked, the sterilization unit 24 is disposed below the floor cloth which is positioned at a lower portion of the mobile robot 1. When two floor cloths are disposed on the left and right sides at the lower portion of the mobile robot 1, two sterilization units 24 may be provided on the left and right sides to correspond to the two floor clothes. In this case, the sterilization units 24 may be symmetrical to each other with respect to the vertical central axis.

Figure 2:
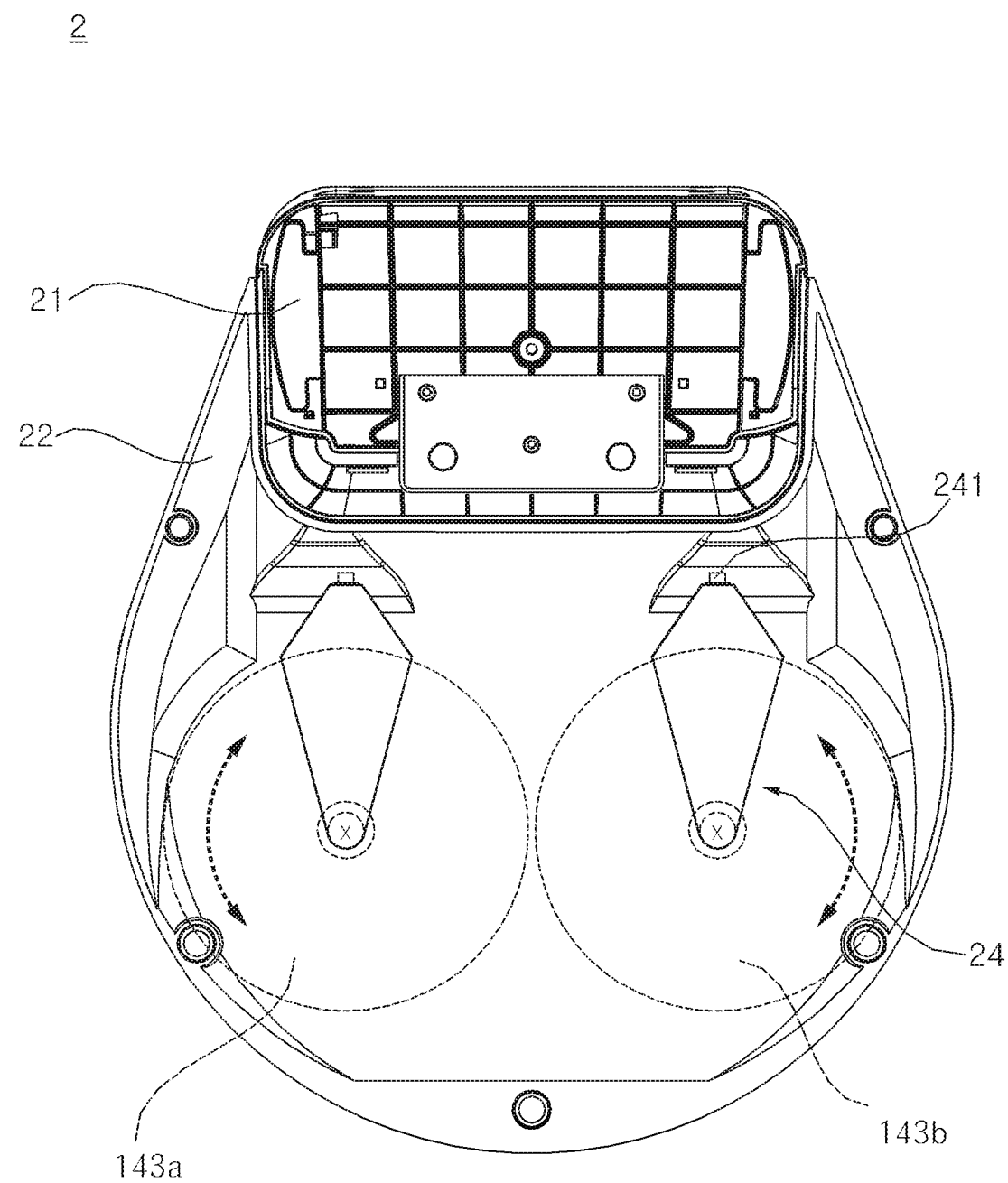
FIG. 2 is a bottom view of a docking apparatus, to which a mobile robot is docked.

FIG. 2 is a bottom view of the docking apparatus 2, which is viewed from the bottom when the mobile robot 1 is docked thereto. The sterilization unit 24 vertically overlaps the floor cloth disposed at the mobile robot 1. The sterilization unit 24 may emit germicidal light to an area, facing the floor cloth, to sterilize the floor cloth.

A rear end of the sterilization unit 24 may be disposed at the center of rotation of the floor cloth. A left surface of a right surface of the sterilization unit 24 may extend from the rear end of the sterilization unit 24 in a radial direction of the floor cloth. Accordingly, an overlapping region of the sterilization unit 24 and the floor cloth has a fan shape or a triangular shape, such that as the sterilization unit 24 rotates, germicidal light may be emitted uniformly.

Figure 3:
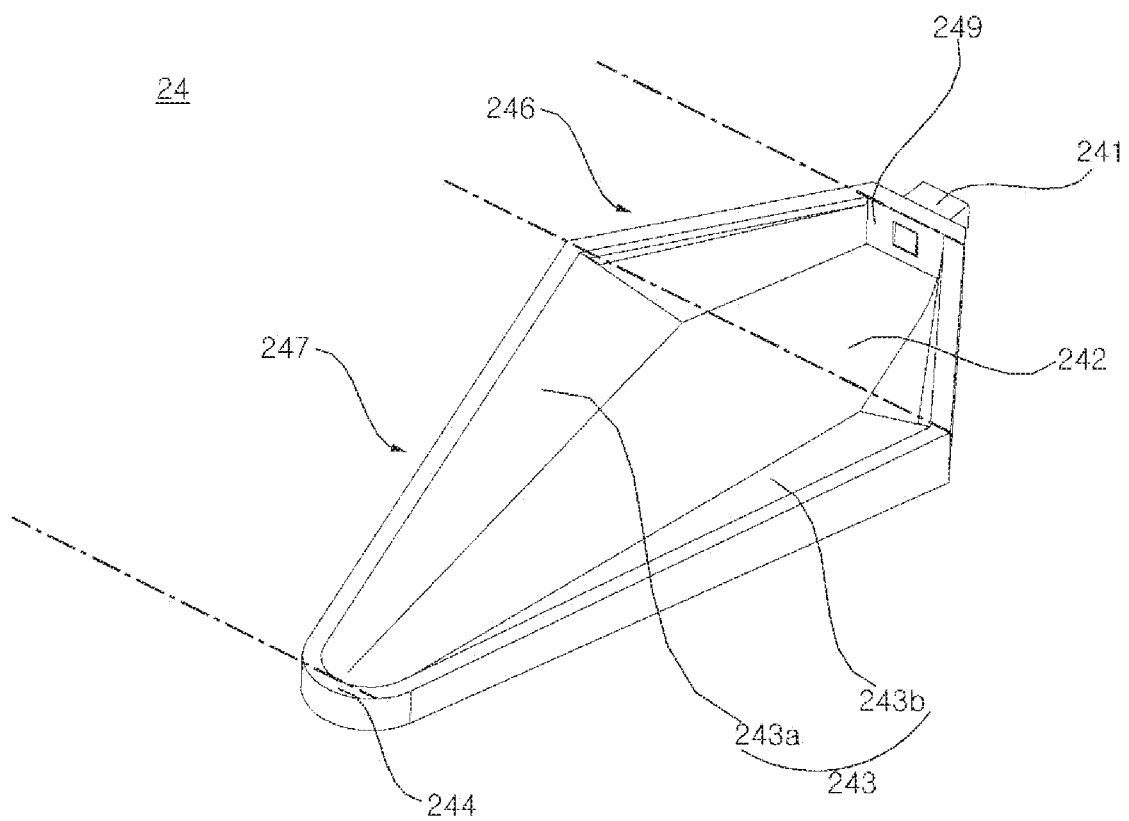
FIG. 3 is a perspective view of a sterilization unit excluding a blocking plate.
Figure 4:
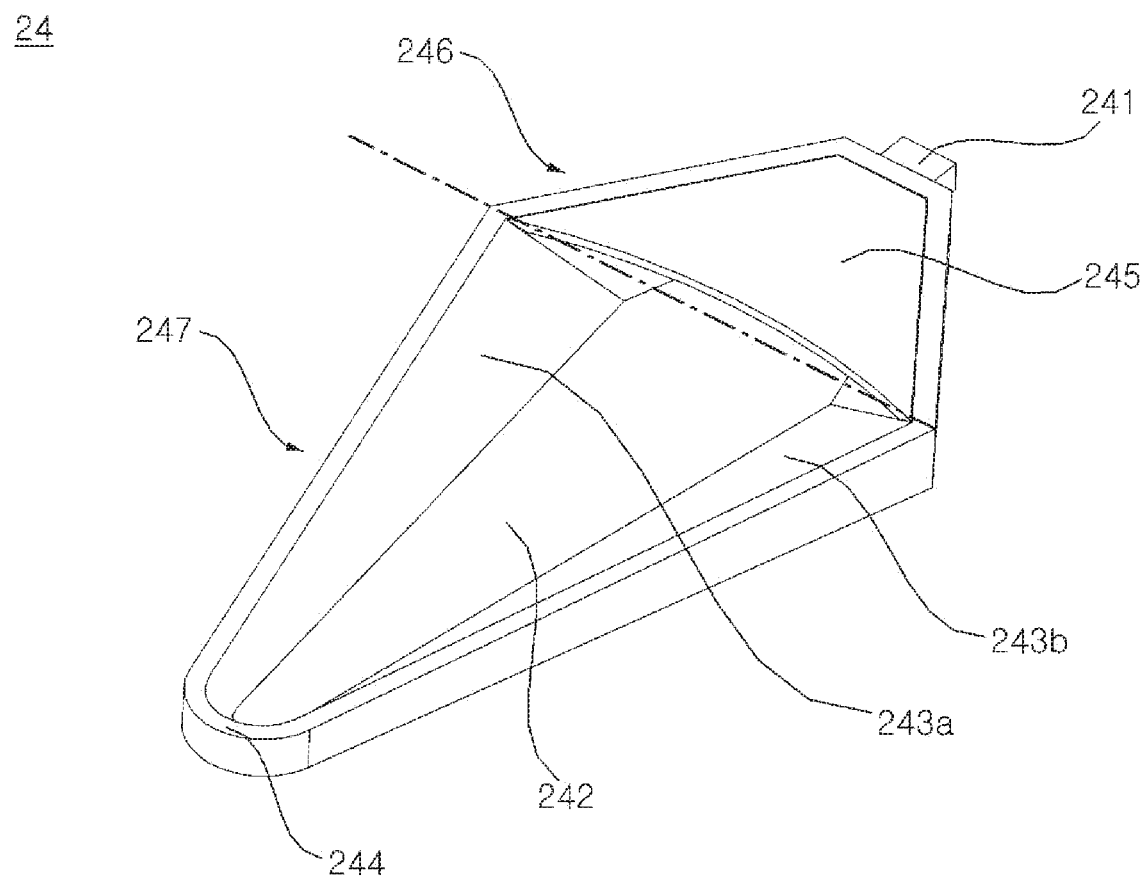
FIG. 4 is a perspective view of a sterilization unit including a blocking plate.

An overall shape of the sterilization unit 24 will be described below with reference to FIG. 3.

The sterilization unit 24 may include a germicidal lamp 241 and a reflection module.

The reflection module has a space, into which germicidal light is emitted, and has a case which surrounds the space. The case of the sterilization unit 24 may be integrally formed with the plate 22, or may be formed separately from the plate 22 and may be connected thereto. A reflecting surface for reflecting the germicidal light is formed on the inside of the case of the sterilization unit 24. The germicidal light is totally reflected by the reflecting surface. The reflection module reflects light, emitted by the germicidal lamp 241, to the upper portion of the plate 22.

For example, the reflection module includes: a light-provided surface 249, to which light of the germicidal lamp 241 is provided; and reflecting plates 242, 243 and 244 which are connected to the light-provided surface 249, and have a wider area than the is provided surface 249, a surface intersecting the light-provided surface 249, and an open upper portion. That is, the germicidal lamp 241 is disposed on one side surface of the reflection module, and the reflection module reflects light of the germicidal lamp 241 to the upper portion of the plate 22. The reflecting plates 242, 243 and 244 are open to the upper portion of the plate 22.

The light-provided surface 249 has a hole 249a, at which the germicidal lamp 241 is positioned. The light-provided surface 249 is disposed parallel to a vertical direction, and the hole 249a formed at the light-provided surface 249 is formed in a horizontal direction.

The reflecting plates 242, 243 and 244 include: a diffusing part 246 having a narrow front portion and a wide rear portion, and a converging part 247 having a wide front portion and a narrow rear portion. Specifically, the reflecting plates 242, 243 and 244 may be divided into: the diffusing part 246, one end of which is connected to the light-provided surface 249, and has a width which increases further away from the light-provided surface 249; and the converging part 247, one end of which is connected to the diffusing part 246, and has a width which decreases further away from the light-provided surface 249.

The diffusing part 246 is a space, in which the light of the germicidal lamp 241, which is point light, is reflected and diffused; and the converging part 247 is a space, in which the light, emitted from the diffusing part 246, is reflected upward. A length of the converging part 247 is preferably greater than a length of the converging part 246 for diffusion of light.

The overall shape of the sterilization unit 24 may be a diamond shape or an elliptical shape, and may include changes to a shape which may be adopted by those skilled in the art.

While the diffusing part 246 does not vertically overlap with the floor cloth, the converging part 247 may vertically overlap with the floor cloth. A blocking plate 245 is disposed at an upper portion of the diffusion part 246 such that the germicidal light is not emitted upward, while the upper portion of the converging part 247 is open to allow the germicidal light to be emitted upward.

The diffusing part 246 diffuses the germicidal light, and delivers the light to the converging part 247. When viewed from the rear, a cross-sectional area of the diffusing part 246 may increase from the front to the rear. The germicidal lamp 241 for radiating the germicidal light may be installed at a front end of the diffusing part 246. The reflecting plate disposed at the diffusing part 246 may be horizontal to a radiation direction of the germicidal light. An angle $\theta 4$, formed between the light radiation direction of the germicidal lamp 241 and the reflecting plate disposed at the diffusing part 246, may be an acute angle.

The converging part 247 converges the germicidal light, delivered from the diffusing part 246, and emits the light upward. The converging part 247 may vertically overlap with a portion of the floor cloth. When viewed from the rear, a cross-sectional area of the converging part 247 may decrease gradually from the front to the rear. The reflecting plate disposed at the converging part 247 may be horizontal to the radiation direction of the germicidal light. An angle, formed between the light radiation direction of the germicidal lamp 241 and the reflecting plate disposed at the converging part 247, may be an obtuse angle. The reflecting plates 242, 243 and 244 extend from the center of rotation of the floor cloth in a radial direction. The light-provided surface 249 of the reflecting plates 242, 243 and 244 is disposed at a position which is farthest away from the center of rotation of the floor cloth, and the other end of the converging part 247 may be disposed at the center of rotation of the floor cloth.

Figure 5:
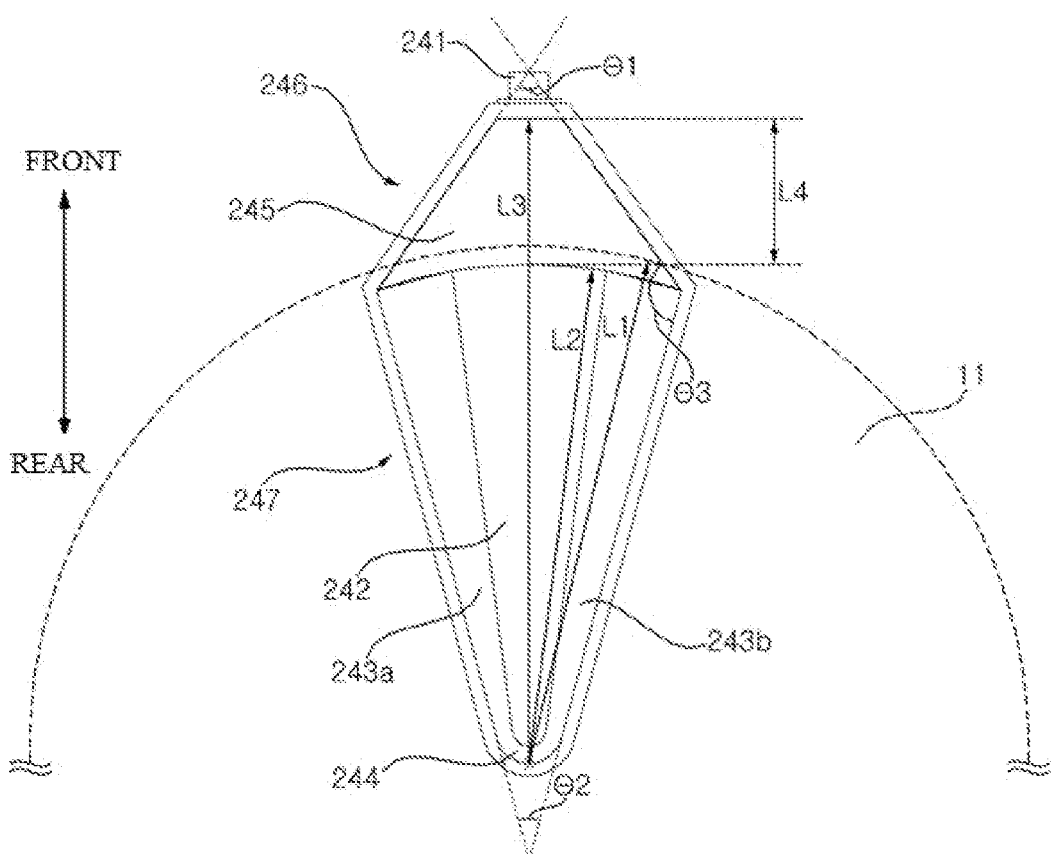
FIG. 5 is a plan view of a sterilization unit.

Referring to FIG. 5, a longitudinal length L2 of the converging part 247 may be equal to a length L1 of a radius of a circular floor cloth, or may be greater than the length L1 of the radius of the circular floor cloth. The longitudinal length L2 of the converging part 247 may not be longer than a shortest distance between the center of rotation and the end of the floor cloth (not shown). Accordingly, when the floor cloth makes one rotation, the entire floor cloth is sterilized. The spin mop 141 rotates about a rotational axis which is parallel to a direction in which the spin mop 141 intersects with the upper surface of the plate 22. It is preferred that the spin mop 141 rotates about a rotational axis parallel to a direction which is perpendicular to the upper surface of the plate 22.

The reflecting plates 242, 243 and 244 may include: the lower reflecting plate 242 which has a surface parallel to the upper surface of the plate 22, and is disposed below the germicidal lamp 241, and the side reflecting plates 243 and 244 which are connected to at least both ends of the lower reflecting plate 242 and have a slope which is inclined upward further away from the lower reflecting plate 242.

A width of the side reflecting plates 243 and 244 may increase further away from the light-provided surface 249, and then may be reduced. A width of the lower reflecting plate 242 may increase further away from the light-provided surface 249, and then may be reduced.

The side reflecting plates 243 and 244 include: the rear reflecting plate 244, which is disposed to face the light-provided surface 249 and is connected to one end of the lower reflecting plate 242, and a left reflecting plate 243a and a right reflecting plate 243b, which are disposed to face each other and are connected to the lower reflecting plate 242 and the rear reflecting plate 244.

When viewed from the top, an angle $\theta 2$ formed between the left reflecting plate 243a and the right reflecting plate 243b may be 30 degrees.

The lower reflecting plate 242 is a reflecting plate which reflects upward the germicidal light which is directed downward. The lower reflecting plate 242 is disposed below the sterilization unit 24. The lower reflecting plate 242 is disposed below the germicidal lamp 241. The lower reflecting plate 242 may be disposed over the diffusing part 246 and the converging part 247. The lower reflecting plate 242, disposed at the diffusing part 246, has a narrow front portion and a wide rear portion, and the lower reflecting plate 242, disposed at the converging part 247, has a wide front portion and a narrow rear portion.

When viewed from the top, the lower reflecting plate 242, which is exposed except for a region which is shielded by the blocking plate 245, may have a wide front portion and a narrow rear portion. Accordingly, when the circular floor cloth makes one rotation, the entire portions of the floor cloth may be uniformly exposed to the germicidal light during a predetermined period of time.

The lower reflecting plate 242 may be parallel to a light radiation direction D1. More specifically, the lower reflecting plate 242 may be parallel to the floor surface. As the lower reflecting plate 242 may be parallel to the floor surface, germicidal light may be emitted uniformly to the left and right sides.

In another example, the lower reflecting plate 242 is divided into the diffusing part 246 and the converging part 247, in which when viewed from the right side, an angle $\theta 4$ formed between the lower reflecting plate 242 of the diffusing part 246 and the radiation direction of the germicidal light may be an acute angle; and an angle formed between the lower reflecting plate 242 of the converging part 247 and the radiation direction of the germicidal light may be an obtuse angle. In this case, the lower reflecting plate 242 of the diffusing part 246 is inclined such that a larger amount of germicidal light may be emitted compared to a case where the reflecting plate is disposed horizontally. An angle formed between the floor surface and the lower reflecting plate 242 of the diffusing part 246 may be shallower than an angle formed between the floor surface and the radiation direction of the germicidal light.

The side reflecting plate 243 is a reflecting plate for reflecting the germicidal light, which is directed to the side, toward the center or the top. The side reflecting plate 243 may be disposed at one side, or both sides, of the lower reflecting plate 242. The side reflecting plate 243 may be disposed at one side, or both sides, of the germicidal lamp 241. The side reflecting plate 243 may be disposed over the diffusing part 246 and the converging part 247. The side reflecting plate 243, disposed at the diffusing part 246, has a narrow front portion and a wide rear portion, and the side reflecting plate 243, disposed at the converging part 247, has a wide front portion and a narrow rear portion.

The side reflecting plate 243 may be inclined upward from the lower reflecting plate 242. The side reflecting plate 243 may be perpendicular to the lower reflecting plate 242 (not shown). As the side reflecting plate 243 is inclined from the lower reflecting plate 242 or is perpendicular to the lower reflecting plate 242, the germicidal light, which is directed toward the side, may be reflected to the center or the top to be concentrated.

When viewed from the top, the side reflecting plate 243, which is exposed except for a region which is shielded by the blocking plate 245, may have a wide front portion and a narrow rear portion. Accordingly, when viewed from the top, the cross section of the side reflecting plate 243 has a triangular shape or a fan shape, such that when the circular floor cloth makes one rotation, the entire portions of the floor cloth may be uniformly exposed to the germicidal light during a predetermined period of time.

When viewed from the top, an angle θ3 formed between the side reflecting plate 243 of the diffusing part 246 and the side reflecting plate 243 of the converging part 247 may be 180 degrees or less. The side reflecting plate 243 of the diffusing part 246 may be disposed to be away from the radiation direction of the germicidal light, and the side reflecting plate 243 of the converging part 247 may be disposed to be close to the radiation direction of the germicidal light.

When viewed from the top, an angle θ2 formed between the left reflecting plate 243*a* and the right reflecting plate 243*b* with respect to the rear reflecting plate 244 may be an acute angle. More specifically, when viewed from the top, the angle θ2 formed between a left end of the left reflecting plate 243*a* and a right end of the right reflecting plate 243*b* with respect to the rear reflecting surface 244 may be an acute angle, and may be preferably in a range of 27 degrees to 33 degrees. When viewed from the top, an angle θ1 formed between the left reflecting plate 243*a* and the right reflecting plate 243*b* with respect to the germicidal lamp 241 may be greater than the angle θ2 formed between the left reflecting plate 243*a* and the right reflecting plate 243*b* with respect to the rear reflecting plate 244.

The rear reflecting plate 244 may be disposed to correspond to the position of the germicidal lamp 241. That is, the rear reflecting plat 244 is disposed at a rear end of the sterilization unit 24, and may be disposed in the radiation direction of the germicidal light of the germicidal lamp 241 when viewed from the top.

A rear end of the rear reflecting plate 244 is connected to a rear end of the lower reflecting plate 242. The rear reflecting plate 244 is inclined upward from the lower reflecting plate 242, so as to reflect the germicidal light upward.

Both side ends of the rear reflecting plate 244 are connected respectively to both side reflecting plates 243, thereby reflecting the reflected germicidal light to an upper central portion.

The rear reflecting plate 244 may be provided separately from the side reflecting plate 243 and may be connected thereto, or may be integrally formed with the side reflecting plate 243. The rear reflecting plate 244 may be provided separately from the lower reflecting plate 242 and may be connected thereto, or may be integrally formed with the lower reflecting plate 242.

The rear reflecting plate 244 may have a curved surface. The center of rotation of the mop module 14 may vertically coincide with a center of curvature of the rear reflecting plate 244.

The blocking plate 245 shields germicidal light which leaks to the floor cloth or to the outside. The blocking plate 245 covers the upper portion of the diffusing part 246. The blocking plate 245 may also be disposed on an upper portion of the germicidal lamp 241.

The blocking plate 245, which is a device for absorbing ultraviolet (UV) light, may be made of a plate, to which a UV absorbent is added, or may be made of a plate which is coated with a UV-absorbing film. The blocking plate 245 may block UVA radiation (315 nm to 380 nm), UVB radiation (280 nm to 315 nm), or UVC radiation (220 nm to 280 nm).

The blocking plate 245 is disposed on an upper portion of the lower reflecting plate 242 or the side reflecting plate 243, to block germicidal light emitted to one region of the upper portion. The blocking plate 245 is spaced apart upward from the lower reflecting plate 242, and vertically overlaps with one region which is adjacent to the germicidal lamp 241 on the lower reflecting plate 242, so as to block light emitted to the region. The blocking plate 245 vertically overlaps with the one region which is adjacent to the germicidal lamp 241 on the side reflecting plate 243, so as to block light emitted to the region.

The blocking plate 245 is spaced apart upward from the lower reflecting plate 242, and may vertically overlap with the diffusing part 246. Accordingly, the light, supplied from the germicidal lamp 241, may be easily diffused to the diffusing part 246 even when a length of the diffusing part 246 is short, and may be supplied to the converging part 247; and then, the light supplied to the converging part 247 may be supplied uniformly to the upper portion of the plate 22.

If the floor cloth vertically overlaps with a portion of the upper side of the sterilization unit 24, the blocking plate 24 may be disposed on an upper side of a region, other than a region facing the floor cloth. Accordingly, the blocking plate 24 may block the germicidal light leaking to a region in which the sterilization unit 24 does not vertically overlap with the floor cloth.

When viewed from the top, the blocking plate 245 may be disposed on an upper side of the diffusing part 246. The floor cloth is disposed on an upper side of the converging part 247 while overlapping therewith, and the germicidal light is emitted upward from the converging part 247 to sterilize the floor cloth, such that the blocking plate 245 may block the germicidal light leaking outside of the floor cloth.

As the germicidal light, UV rays may be used, and preferably UVC rays may be used.

The UV rays may include UVA light (315 nm to 380 nm), UVB light (280 nm to 315 nm), UVC light (220 nm to 280 nm) and the like. Among these UV rays, UVC light has a wavelength which may damage DNA of living organisms, such that the UVC radiation has superior germicidal power to UVA or UVB radiation. Further, a smaller amount of energy is required to emit UVC radiation than UVA or UVB radiation. However, UVC rays are harmful not only to bacteria but also to the human body, such that a long-term exposure to UVC radiation can cause skin cancer and the like.

The germicidal lamp 241 is disposed at the sterilization unit 24, to emit germicidal light into the sterilization unit 24. The germicidal lamp 241 is preferably disposed at a front end of the sterilization unit 24 to emit the germicidal light to a rear end thereof.

The germicidal lamp 241 may emit germicidal light obliquely to the lower reflecting plate 242. By emitting the germicidal light downward, the germicidal lamp 241 may minimize germicidal light absorbed by the blocking plate 245, while maximizing germicidal light emitted to the outside.

The germicidal lamp 241 may emit germicidal light to a distance which is longer than a half of a longitudinal length of the blocking plate 245. A radiation direction of the germicidal light may be disposed to reach the floor cloth when the germicidal light is emitted once.

Referring to FIG. 2, when the mobile robot 1 is docked to the docking apparatus 2, the floor cloth and the sterilization unit 24 vertically overlap with each other. More specifically, the converging part 247 of the sterilization unit 24 is disposed to vertically overlap with the floor cloth, and the diffusing part 246 of the sterilization unit 24 does not vertically overlap with the floor cloth.

A method of operating the aforementioned sterilization unit 24 will be described below.

Once the mobile robot 1 is docked to a dock disposed on an upper portion of the docking apparatus 2, the sterilization unit 24 operates according to instructions of the controller.

The germicidal lamp 241, disposed on a front end of the diffusing part 246 of the sterilization unit 24, emits germicidal light to a rear end of the diffusing part 246. A cross-sectional area of the diffusing part 246 increases toward the rear end thereof, such that the emitted germicidal light is diffused toward the rear end while being reflected repeatedly.

The converging part 247 is disposed at the rear end of the diffusing part 246. A cross-sectional area of the converging part 247 decreases toward a rear end thereof, such that the emitted germicidal light converges toward the rear end while being reflected repeatedly, and may be emitted uniformly onto the lower reflecting plate 242, the side reflecting plate 243 and the rear reflecting plate 244. The germicidal light is emitted to the outside through an upper opening of the converging part 247. The germicidal light emitted to the outside sterilizes one region of the floor cloth positioned at an upper portion.

The floor cloth having a circular shape may rotate transversely. If the germicidal light sterilizes one region, and the entire region of the floor cloth may be sterilized uniformly by making one transverse rotation.

In one embodiment, if an angle θ2 at the rear end of the sterilization unit 24 is 30 degrees, the entire surface of the floor cloth may be sterilized by emitting germicidal light twelve times while the floor cloth makes one rotation.

When a bottom surface of the pair of spin mops 41a and 41b, which are symmetrical to each other with respect to the central vertical line Po, are horizontal to a horizontal plane, the robot cleaner may not travel in a stable manner, and it is difficult to control traveling of the robot cleaner. Accordingly, in the present disclosure, each spin mop 41 is inclined downward toward an outer front side thereof. The slope and motion of the spin mop 41 will be described below.

The central vertical line Po refers to a line which is parallel to a front-rear direction, and passes the center of a geometric center Tc of the body 13. In this case, the central vertical line Po may be defined as a line which vertically intersects with a virtual line, formed by connecting a central axis of the left spin mop and a central axis of the right spin mop, and which passes the center of the geometric center Tc of the body 13.

Figure 6:
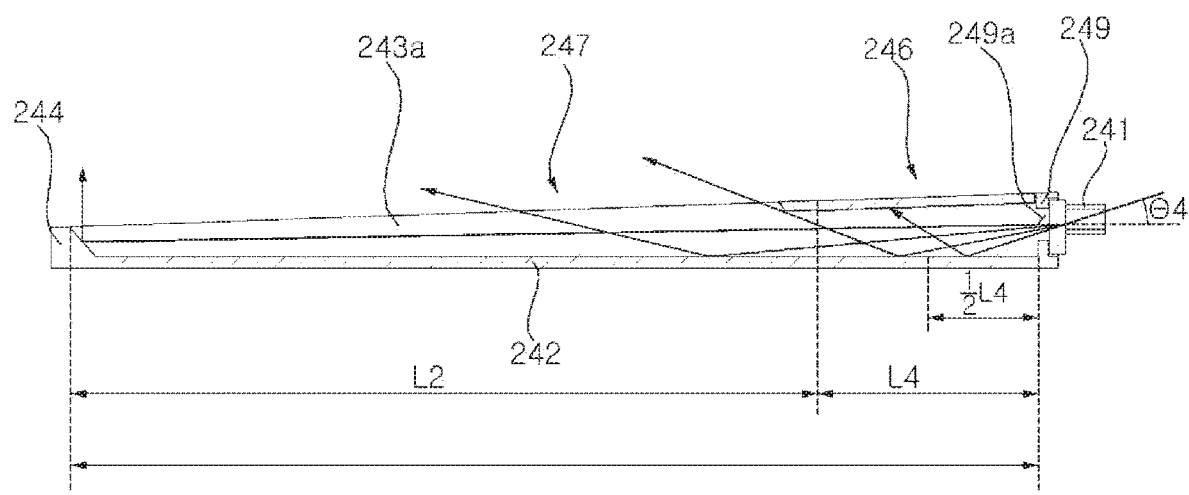
FIG. 6 is a right cross-sectional view of a sterilization unit.
Figure 7:
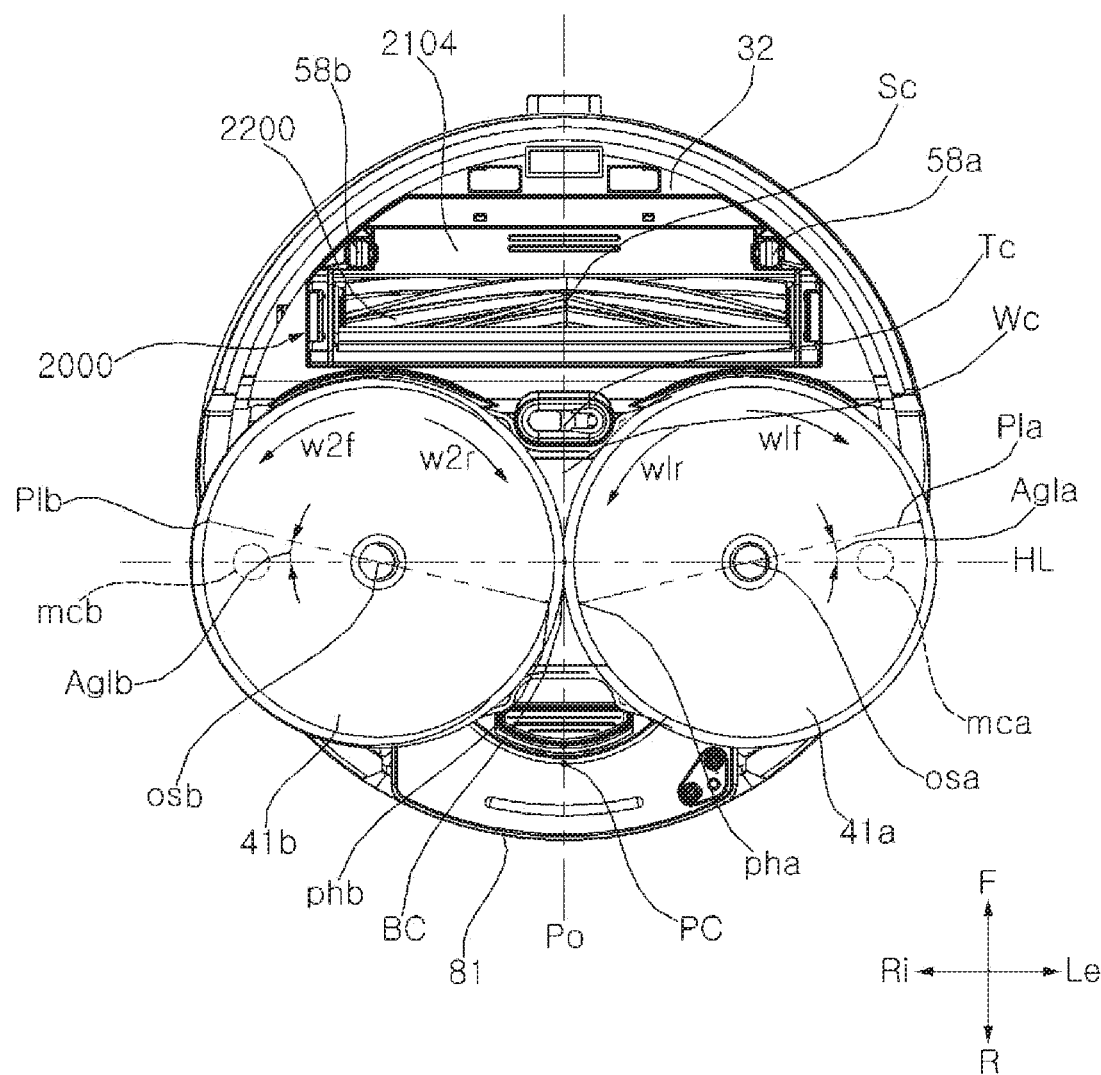
FIG. 7 is a bottom view of FIG. 1, explaining a center of mass according to an embodiment of the present disclosure and a lowest end of a spin mop.

FIG. 7 illustrates a point, at which a spin shaft Osa and a lower surface of the left spin mop 41a intersect, and a point at which a spin shaft Osb and a lower surface of the right spin mop 41b intersect. When viewed from the bottom, a direction in which the left spin mop 41a spins clockwise is defined as a first forward direction w1f, and a direction in which the left spin mop 41a spins counter-clockwise is defined as a first reverse direction w1r. When viewed from the bottom, a direction in which the right spin mop 41b spins counter-clockwise is defined as a second forward direction w2f, and a direction in which the right spin mop 41b spins clockwise is defined as a second reverse direction w2r. Further, when viewed from the bottom, "an acute angle, formed between a tilt direction of the lower surface of the left spin mop 41a and a left-right axis thereof," and "an acute angle, formed between a tilt direction of the lower surface of the right spin mop 41b and a left-right axis thereof," are defined as tilt direction angles Ag1a and Ag1b. The tilt direction angle Ag1a of the left spin mop 41a may be equal to the tilt direction angle Ag1b of the right spin mop 41b. Further, referring to FIG. 6, "an angle of the lower surface I of the left spin mop 41a with respect to a virtual horizontal plane H" and "an angle of the lower surface I of the right spin mop 41b with respect to a virtual horizontal plane H" are defined as tilt angles Ag2a and Ag2b.

In this case, a right end of the left spin mop 41a and a left end of the right spin mop 41b may come into contact with, or may be adjacent to, each other. Accordingly, a gap in mopping between the left spin mop 41a and the right spin mop 41b may be reduced.

When the left spin mop 41a spins, a point Pla of the lower surface of the left spin mop 41a, to which a maximum frictional force is applied from the floor, is located on the left side of a center of rotation Osa of the left spin mop 41a. As a greater load is transmitted to a ground surface at the point Pla of the lower surface of the left spin mop 41a than other points, the maximum frictional force may be generated at the point Pla. In the embodiment, the point Pla is located at a front left side of the center of rotation Osa, but in another embodiment, the point Pla may be disposed exactly at the left side or at the rear left side with respect to the center of rotation Osa.

When the right spin mop 41b spins, a point Plb of the lower surface of the right spin mop 41b, to which a maximum frictional force is applied from the floor, is located at the right side of a center of rotation Osb of the right spin mop 41b. As a greater load is transmitted to a ground surface at the point Plb of the lower surface of the right spin mop 41b than other points, the maximum frictional force may be generated at the point Plb. In the embodiment, the point Plb is located at a front right side of the center of rotation Osb, but in another embodiment, the point Plb may be disposed exactly at the right side or at the rear right side with respect to the center of rotation Osb.

The lower surface of the left spin mop 41a and the lower surface of the right spin mop 41b may be tilted. The tilt angles Ag2a and Ag2b of the left spin mop 41a and the right spin mop 41b may form an acute angle. The tilt angles Ag2a and Ag2b are at the points P1a and P1b, at which the maximum frictional force is exerted, and the entire lower area of the floor cloth 411 may be formed in a small size to touch the floor during spinning of the left spin mop 41a and the right spin mop 41b.

The overall lower surface of the left spin mop 41a is inclined leftwards and downwards. The overall lower surface of the right spin mop 41b is inclined rightwards and downwards. Referring to FIG. 6, the lower surface of the left spin mop 41a has a lowest point P1a on the left side. The lower surface of the left spin mop 41a has a highest point Pha on the right side. The lower surface of the right spin mop 41b has a lowest point P1b on the right side. The lower surface of the right spin mop 41b has a highest point Phb on the left side.

Depending on embodiments, the tilt direction angles Ag1a and Ag1b may be zero degrees. Further, depending on embodiments, when viewed from the bottom, a tilt direction of the lower surface of the left spin mop 41a may form the tilt direction angle Ag1a in a clockwise direction with respect to the left-right axis, and a tilt direction of the lower surface of the right spin mop 41b may form the tilt direction angle Ag1b in a counter-clockwise direction with respect to the left-right axis. In the embodiment of the present disclosure, when viewed from the bottom, a tilt direction of the lower surface of the left spin mop 41a may form the tilt direction angle Ag1a in a counter-clockwise direction with respect to the left-right axis, and a tilt direction of the lower surface of the right spin mop 41b may form the tilt direction angle Ag1b in a clockwise direction with respect to the left-right axis.

The cleaner 1 moves by a frictional force with a ground surface, which is generated by the mop module 40.

The mop module 40 may generate "a forward movement frictional force" for moving the body 30 forward, or a "rearward movement frictional force" for moving the body 30 backwards. The mop module 40 may generate a "leftward moment frictional force" for turning the body 30 to the left, or a "rightward moment frictional force" for turning the body 30 to the right. The mop module 40 may generate a frictional force by combining any one of the forward movement frictional force and the rearward movement frictional force with any one of the leftward moment frictional force and the rightward moment frictional force.

In order for the mop module 40 to generate the forward movement frictional force, the left spin mop 41a spins at a predetermined rpm R1 in the first forward direction w1f, and the right spin mop 41b spins at the predetermined rpm R1 in the second forward direction w2f.

In order for the mop module 40 to generate the rearward movement frictional force, the left spin mop 41a spins at a predetermined rpm R2 in the first reverse direction w1r, and the right spin mop 41b spins at the predetermined rpm R2 in the second reverse direction w2f.

In order for the mop module 40 to generate the rightward moment frictional force, the left spin mop 41a spins at a predetermined rpm R3 in the first forward direction w1f, and the right spin mop 41b (i) spins in the second reverse direction w2r, (ii) is stopped without spinning, or (iii) spins at an rpm R4, which is less than the rpm R3, in the second forward direction w2f.

In order for the mop module 40 to generate the leftward moment frictional force, the right spin mop 41b spins at a predetermined rpm R5 in the second forward direction w2f, and the left spin mop 41a (i) spins in the first reverse direction w1f, (ii) is stopped without spinning, or (iii) spins at an rpm R6, which is less than the rpm R5, in the first forward direction w1f.

Hereinafter, an arrangement of each element for improving stability in a left-right direction and a front-rear direction while increasing a frictional force of the spin mops 41 located at the left and right sides, and allowing safe traveling regardless of a water level in a water tank 81.

Figure 8:
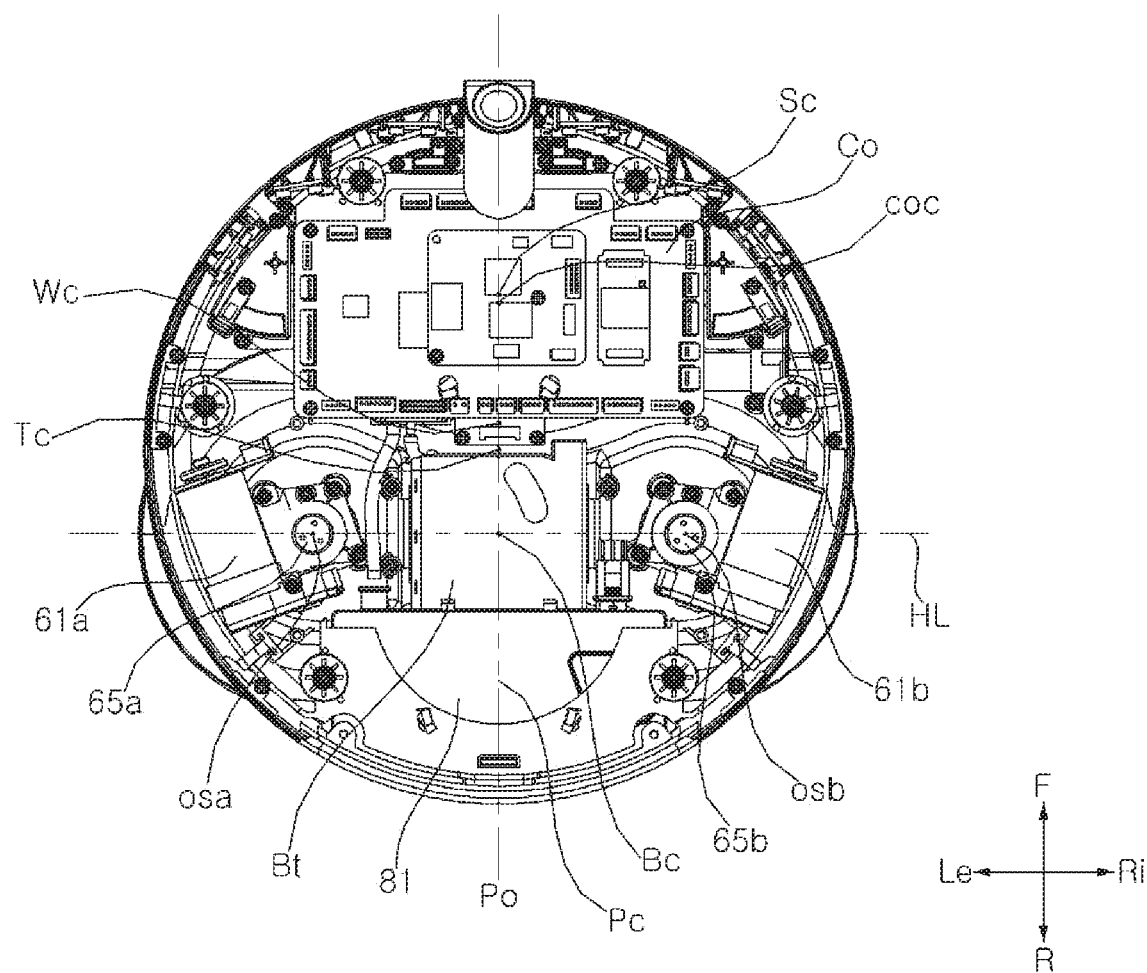
FIG. 8 is a plan view of a center of mass as seen from above, in which a case is removed from a body in FIG. 1.

Referring to FIGS. 7 and 8, in order to increase a frictional force of the spin mop 41 and to prevent eccentricity from occurring in one direction when the mobile robot rotates, a battery Bt and the mop motor 61, which are relatively heavy, may be disposed at the top of the spin mop 41.

Specifically, the left mop motor 61a is disposed above the left spin mop 41a, and the right mop motor 61b is disposed above the right spin mop 41b. That is, at least a portion of the left mop motor 61a may overlap vertically with the left spin mop 41a. It is preferred that the entire portion of the left mop motor 61a may overlap vertically with the left spin mop 41a. At least a portion of the right mop motor 61b may overlap vertically with the right spin mop 41b. It is preferred that the entire portion of the right mop motor 61b may overlap vertically with the right spin mop 41b.

More specifically, the left mop motor 61a and the right mop motor 61b may overlap vertically with a virtual central horizontal line HL, formed by connecting the spin shaft Osa of the left spin mop 41a and the spin shaft Osb of the right spin mop 41b. It is preferred that a center of mass MCa of the left mop motor 61a and a center of mass MCb of the right mop motor 61b may overlap vertically with the virtual central horizontal line HL which is formed by connecting the spin shaft Osa of the left spin mop 41a and the spin shaft Osb of the right spin mop 41b. Alternatively, a geometric center of the left mop motor 61a and a geometric center of the right mop motor 61b may overlap vertically with the virtual central horizontal line HL which is formed by connecting the spin shaft Osa of the left spin mop 41a and the spin shaft Osb of the right spin mop 41b. In this case, the left mop motor 61a and the right mop motor 61b are symmetrical to each other with respect to a central vertical line Po of the robot cleaner.

As the center of mass MCa of the left mop motor 61a and the center of mass MCb of the right mop motor 61b are symmetrical to each other without deviating from each spin mop 41, a frictional force of the spin mop 41 may increase, and driving performance and horizontal balance may be maintained.

Hereinafter, the spin shaft OSa of the left spin mop 41a is defined as a left spin shaft Osa, and the spin shaft Osb of the right spin mop 41b is defined as a right spin shaft Osb.

As the water tank 81 is disposed behind the central horizontal line HL, and the amount of water in the water tank 81 is variable, the left mop motor 61a may be biased leftward from the left spin shaft Osa in order to maintain a stable balance in the front-rear direction regardless of a water level in the water tank 81. The left mop motor 61a may be biased to the front left side from the left spin shaft Osa. It is preferred that the geometric center or the center of mass MCa of the left mop motor 61a is biased leftward from the left spin shaft Osa, or the geometric center or the center of mass MCa of the left mop motor 61a is biased to the front left side from the left spin shaft Osa.

The right mop motor 61b may be biased rightward from the right spin shaft Osb. The right mop motor 61b may be biased to the front right side from the right spin shaft Osb.

It is preferred that the geometric center or the center of mass MCb of the right mop motor 61*b* is biased rightward from the right spin shaft Osb, or the geometric center or the center of mass MCb of the right mop motor 61*b* is biased to the front right side from the right spin shaft Osb.

As the left mop motor 61*a* and the right mop motor 61*b* apply pressure at positions which are biased toward an outer front side from the center of each spin mop 41, the pressure is concentrated on the outer front side of each spin mop 41, such that driving performance may be improved by the rotational force of the spin mop 41.

The left spin shaft Osa and the right spin shaft Osb are disposed behind the center of the body 30. The central horizontal line HL is disposed behind a geometric center of the body 30 and a center of mass WC of the mobile robot. The left spin shaft Osa and the right spin shaft Osb are spaced apart equally from the central vertical line Po of the mobile robot.

A left master joint 65*a* is disposed on the left spin mop 41*a*, and a right master joint 65*b* is disposed on the right spin mop 41*b*.

In the embodiment of the present disclosure, a single battery Bt is installed. At least a portion of the battery Bt is disposed on the left spin mop 41*a* and the right spin mop 41*b*. As the battery Bt, which is relatively heavy, is disposed on the spin mop 41, a frictional force of the spin mop 41 may increase, and eccentricity occurring due to the rotation of the mobile robot may be reduced.

Specifically, a portion of the left side of the battery Bt may vertically overlap with the left spin mop 41*a*, and a portion of the right side of the battery Bt may vertically overlap with the right spin mop 41*b*. The battery Bt may vertically overlap with the central horizontal line HL and may vertically overlap with the central vertical line Po of the mobile robot.

More specifically, a center of mass BC or a geometric center of the battery Bt may be disposed on the central vertical line Po of the mobile robot, and may be disposed on the central horizontal line HL. In this case, the center of mass BC or the geometric center of the battery Bt may be disposed on the central vertical line Po of the mobile robot, may be disposed forward of the central horizontal line HL, or may be disposed behind the geometric center Tc of the body 30.

The center of mass BC or the geometric center of the battery Bt may be disposed forward of the water tank 81 or the center of mass PC of the water tank 81. The center of mass BC or the geometric center of the battery Bt may be disposed behind a center of mass SC of the sweep module 2000.

As one battery Bt is interposed between the left spin mop 41*a* and the right spin mop 41*b*, and is disposed on the central horizontal line HL and the vertical line Po of the mobile robot, the heavy battery Bt maintains the balance during the spinning of the spin mops 41, and puts weight on the spin mops 41, thereby increasing a frictional force of the spin mops 41.

The battery Bt may be disposed at the same height (height of a lower end) as the left mop motor 61*a* and the right mop motor 61*b*. The battery Bt may be interposed between the left mop motor 61*a* and the right mop motor 61*b*. The battery Bt is disposed in an empty space between the left mop motor 61*a* and the right mop motor 61*b*.

At least a portion of the water tank 81 is disposed on the left spin mop 41*a* and the right spin mop 41*b*. The water tank 81 may be disposed behind the central horizontal line HL, and may vertically overlap with the central vertical line Po of the mobile robot.

More specifically, the center of mass PC or a geometric center of the water tank 81 may be disposed on the central vertical line Po of the mobile robot and disposed forward of the central horizontal line HL. In this case, the center of mass PC or the geometric center of the water tank 81 may be disposed on the central vertical line Po of the mobile robot and disposed behind the central horizontal line HL. Here, the position of the center of mass PC or the geometric center of the water tank 81, which is disposed behind the central horizontal line HL, indicates that the center of mass PC or the geometric center of the water tank 81 vertically overlaps with one region which is positioned behind the central horizontal line HL. In this case, the center of mass PC or the geometric center of the water tank 81 may vertically overlap with the body 30 without deviating from the body 30.

The center of mass PC or the geometric center of the water tank 81 may be disposed behind the center of mass BC of the battery Bt. The center of mass PC or the geometric center of the water tank 81 may be disposed behind the center of mass SC of the sweep module 2000.

The water tank 81 may be disposed at the same height (height of a lower end) as the left mop motor 61*a* and the right mop motor 61*b*. The water tank 81 may be disposed behind a space between the left mop motor 61*a* and the right mop motor 61*b*.

The sweep module 2000 is disposed forward of the spin mops 41, the battery Bt, the water tank 81, a mop driving part 60, the right mop motor 61*b*, and the left mop motor 61*a* in the case 30.

The center of mass PC or a geometric center of the sweep module 2000 may be disposed on the central vertical line Po of the mobile robot, and may be disposed forward of the geometric center Tc of the body 30. The body 30 may have a circular shape when viewed from the top, and the base 32 may have a circular shape. The geometric center Tc of the body 30 refers to its center when the body 30 has a circular shape. Specifically, when viewed from the top, the body 30 is a circle with a radius error being less than 3%.

Specifically, the center of mass SC or the geometric center of the sweep module 2000 may be disposed on the central vertical line Po of the mobile robot, and may be disposed forward of the center of mass BC of the battery Bt, the center of mass of PC of the water tank 81, the center of mass MCa of the left mop motor 61*a*, the center of mass MCb of the right mop motor 61*b*, and the center of mass WC of the mobile robot.

It is preferred that the center of mass SC or the geometric center of the sweep module 2000 is disposed forward of the central horizontal line HL and the front end of the spin mops 41.

As described above, the sweep module 2000 has a dust housing 2100 having a storage space 2104, an agitator 2200, and a sweep motor 2330.

The agitator 2200 is rotatably installed in the sweep module 2000, and is disposed behind the storage space 2104, such that the agitator 2200 may maintain a length appropriate to cover the left and right spin mops 41*a* and 41*b*, without protruding outside of the body 30.

A rotational axis of the agitator 2200 is parallel to the central horizontal line HL, and the center of the agitator 2200 is disposed on the virtual vertical line Po of the mobile robot, thereby allowing large foreign materials, introduced by the spin mops 41, to be removed effectively by the agitator 2200. The rotational axis of the agitator 2200 is disposed forward of the geometric center Tc of the body 30. A length of the agitator 2200 is preferably larger than a distance between the left spin shaft Osa and the right spin shaft Osb. The rotational axis of the agitator 2200 may be disposed adjacent to the front end of the spin mop 41.

The dust housing 2100 may further include a left caster 58a and a right caster 58b, which are provided on both ends thereof, and which come into contact with the floor. The left caster 58a and the right caster 58b may roll while being in contact with the floor, and may be moved vertically by an elastic force. The left caster 58a and the right caster 58b support the sweep module 2000 and a portion of the body 30. The left caster 58a and the right caster 58b protrude downward from a lower end of the dust housing 2100.

The left caster 58a and the right caster 58b are disposed parallel to the central horizontal line HL, and may be disposed forward of the central horizontal line HL and the agitator 2200. A virtual line, formed by connecting the left caster 58a and the right caster 58b, may be disposed forward of the central horizontal line HL, the agitator 2200, and the geometric center Tc of the body 30. In this case, the left caster 58a and the right caster 58b may be symmetrical to each other with respect to the central vertical line Po. The left caster 58a and the right caster 58b may be equally spaced apart from the central vertical line Po.

The geometric center Tc of the body 30, the center of mass WC of the mobile robot, the center of mass SC of the sweep module 2000, and the center of mass BC of the battery Bt are disposed in a virtual square, formed by sequentially connecting the left caster 58a, the right caster 58b, the right spin shaft Osb, and the left spin shaft Osa; and the battery Bt, which is relatively heavy, the left spin shaft Osa, and the right spin shaft Osb are disposed adjacent to the central horizontal line HL. In this arrangement, a primary load of the mobile robot is applied to the spin mops 41, and a remaining secondary load is applied to the left caster 58a and the right caster 58b.

If the sweep motor 2330 is disposed on the central vertical line Po, or if the sweep motor 2330 is disposed on one side with respect to the central vertical line Po of the mobile robot, the pump 85 is disposed on the other side (see FIG. 19), such that a combined center of mass of the sweep motor 2330 and the pump 85 may be disposed on the central vertical line Po.

Accordingly, the center of mass of the mobile robot, which is biased forward, may be maintained regardless of a water level in the water tank 81 which is disposed rearward. In this case, while increasing a frictional force of the spin mop 41, the center of mass WC of the mobile robot may be positioned near the geometric center Tc of the body 30, thereby enabling stable movement.

A center of mass COC or a geometric center of a controller Co may be disposed forward of the geometric center Tc of the body 30 and the central horizontal line HL. At least 50% or more of the controller Co may vertically overlap with the sweep module 2000.

The center of mass WC of the mobile robot may be disposed on the central vertical line Po of the mobile robot; may be disposed forward of the central horizontal line HL; may be disposed forward of the center of mass BC of the battery BC; may be disposed forward of the center of mass PC of the water tank 81; may be disposed behind the center of mass SC of the sweep module 2000; and may be disposed behind the left caster 58a and the right caster 58b.

These elements may be disposed to be symmetrical to each other with respect to the central vertical line Po, or may be disposed by considering their weight, such that the center of mass WC of the mobile robot may be positioned on the central vertical line Po of the mobile robot. When the center of mass WC of the mobile robot is positioned on the central vertical line Po of the mobile robot, there is an effect of improving stability in a left-right direction.

Figure 9:
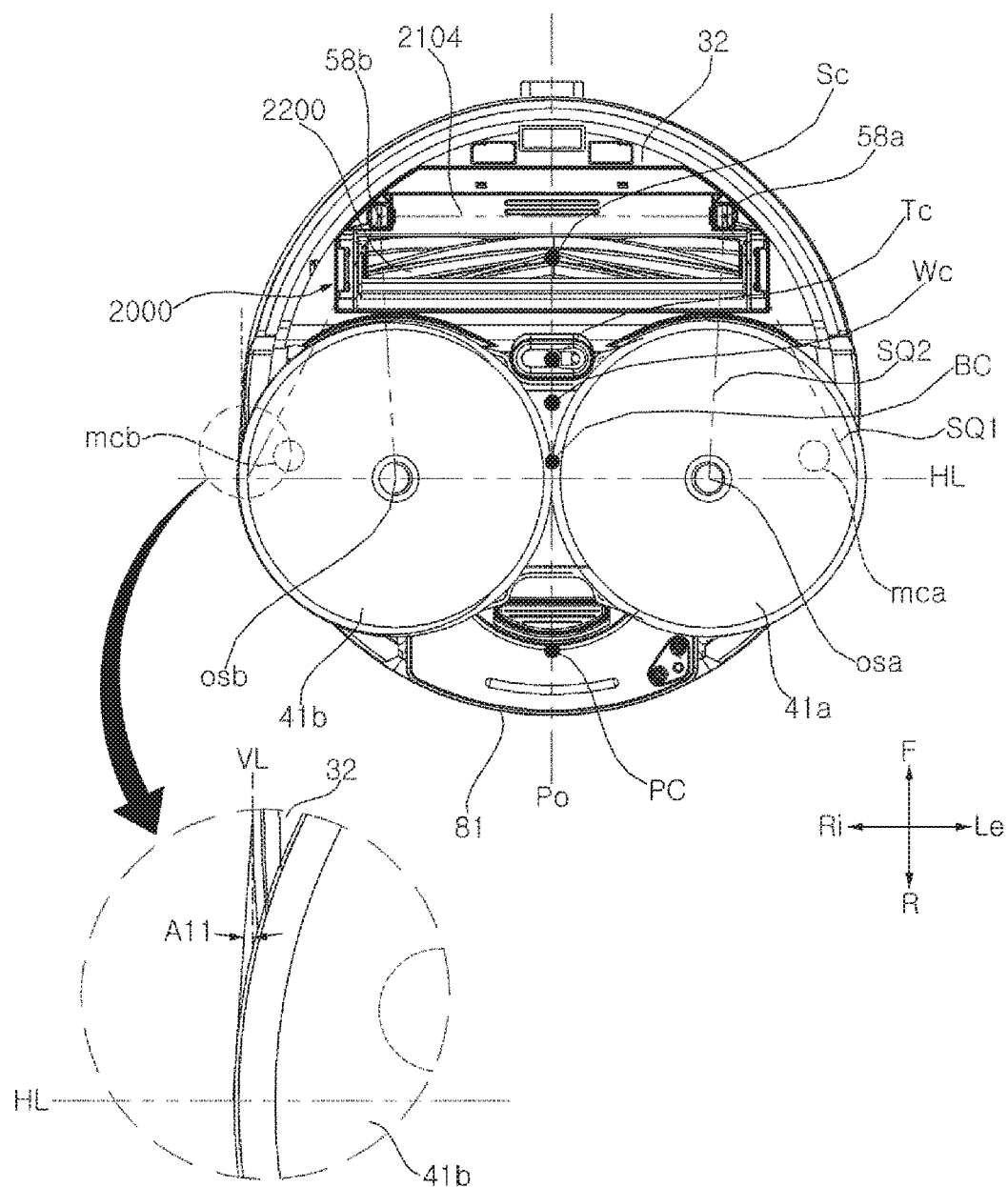
FIG. 9 is a bottom view of FIG. 1, explaining a relationship between a center of mass according to another embodiment of the present disclosure and other elements.

FIG. 9 is a bottom view of FIG. 1, explaining a relationship between a center of mass according to another embodiment of the present disclosure and other elements.

Referring to FIG. 9, the embodiment illustrated in FIG. 9 will be described below based on differences from the embodiment of FIG. 7. Elements not specifically described in FIG. 9 are considered to be the same as FIG. 7.

The center of mass WC of the mobile robot and the geometric center Tc of the body are located in a virtual second quadrant SQ2, which is formed by sequentially connecting the left caster 58a, the right caster 58b, the right spin shaft Osb, and the left spin shaft Osa. The center of mass MCa of the left mop motor, the center of mass MCb of the right mop motor, and the center of mass PC of the water tank may be located outside of the second quadrant SQ2.

Further, the center of mass WC of the mobile robot, the geometric center Tc of the body, and the center of mass BC of the battery Bt are located in the virtual second quadrant SQ2, which is formed by sequentially connecting the left caster 58a, the right caster 58b, the right spin shaft Osb, and the left spin shaft Osa.

In addition, the center of mass WC of the mobile robot, the geometric center Tc of the body, and the center of mass SC of the sweep module 2000 are located in the virtual second quadrant SQ2, which is formed by sequentially connecting the left caster 58a, the right caster 58b, the right spin shaft Osb, and the left spin shaft Osa.

Moreover, the center of mass WC of the mobile robot, the geometric center Tc of the body, the center of mass SC of the sweep module 2000, and the center of mass BC of the battery Bt are located in the virtual second quadrant SQ2, which is formed by sequentially connecting the left caster 58a, the right caster 58b, the right spin shaft Osb, and the left spin shaft Osa.

The center of mass WC of the mobile robot, the geometric center Tc of the body, the center of mass SC of the sweep module 2000, and the center of mass BC of the battery Bt are located in the second quadrant SQ2, while the center of mass MCa of the left mop motor and the center of mass MCb of the right mop motor are located outside of the second quadrant SQ2. Accordingly, the mobile robot may travel in a stable manner, and a proper frictional force may be applied to the floor cloth.

The center of mass WC of the mobile robot and the geometric center Tc of the body are located in the second quadrant SQ2, while the center of mass MCa of the left mop motor and the center of mass MCb of the right mop motor are located outside of the second quadrant SQ2. Accordingly, the mobile robot may travel in a stable manner, and a proper frictional force may be applied to the floor cloth.

The center of mass WC of the mobile robot and the geometric center Tc of the body are located in a virtual first quadrant SQ1, which is formed by sequentially connecting the left caster 58a, the right caster 58b, a lowest point of a lower surface of the right spin mop 41b, and a lowest point of a lower surface of the left spin mop 41a. The center of mass MCa of the left mop motor and the center of mass MCb of the right mop motor may be located outside of the first quadrant SQ1.

A percentage of the overlapping portion of the left spin mop 41a and the right spin mop 41b with the body 30 is preferably in a range of 85% to 95% of each spin mop 41. Specifically, an included angle A11 between a line L11, formed by connecting the right end of the body 30 and the right end of the right spin mop 41b, and a vertical line VL, formed by horizontally connecting the right end of the body 30 and the central vertical line Po, may be in a range of zero degrees to five degrees.

A length of a region of each spin mop 41, which is exposed outside of the body 30, is preferably in a range of ½ to ⅐ of a radius of each spin mop 41. The length of the region of each spin mop 41, which is exposed outside of the body 30, may refer to a distance between one end of each pin mop 41, which is exposed outside of the body 30, to the spin shaft of each spin mop 41.

A distance between the end of the region of each spin mop 41, which is exposed outside of the body 30, and the geometric center Tc of the body 30 may be greater than a mean radius of the body 30.

By considering a relationship with the sweep module 2000, a position, at which each spin mop 41 is exposed, is between a side portion and a rear portion of the body 30. That is, if quadrants are sequentially positioned in a clockwise direction when the body 30 is viewed from below, the position, at which each spin mop 41 is exposed, may be located in the second quadrant or the third quadrant.

According to the present disclosure, the docking apparatus for the mobile robot has one or more of the following effects.

Firstly, when viewed from the top, an angle formed between the left reflecting plate and the right reflecting plate may be an acute angle, such that a radiation region of germicidal light has a triangular shape or a fan shape, thereby allowing the germicidal light to be emitted uniformly.

Secondly, when viewed from the top, the sterilization unit has the diffusing part, in which the germicidal light is diffused, and the converging part, in which the diffused germicidal light converges, thereby allowing the germicidal light to be emitted uniformly.

Thirdly, the blocking plate may be disposed in a region, in which the floor mop and the reflecting plates do not overlap each other, such that leaking germicidal light may be blocked.

However, the effects of the present disclosure are not limited to the aforesaid, and other effects not described herein will be clearly understood by those skilled in the art from the following description of the appended claims.

While the present disclosure has been shown and described with reference to the preferred embodiments thereof, it should be understood that the present disclosure is not limited to the aforementioned specific embodiments, and various modifications and variations may be made by those skilled in the art without departing from the scope and spirit of the disclosure as defined by the appended claims, and the modified implementations should not be construed independently of the technical idea or prospect of the present disclosure.

What is claimed is:

1. A docking apparatus for a mobile robot, the docking apparatus comprising:
    a main body including a power module;
    a plate connected to a lower end of the main body, and including a space for docking the mobile robot; and
    a sterilization unit disposed inside the plate and configured to emit germicidal light onto an upper portion of the plate, the sterilization unit comprising:
        a germicidal lamp for emitting the germicidal light; and
        a reflection module configured to reflect the germicidal light, emitted from the germicidal lamp, onto the upper portion of the plate,
    wherein the reflection module comprises:
        an illuminated surface, illuminated by the germicidal lamp; and
        reflecting plates connected to the illuminated surface and configured to reflect the germicidal light of the germicidal lamp, the reflecting plates having an area wider than both the illuminated surface and a surface intersecting the illuminated surface.

2. The docking apparatus of claim 1, wherein the reflecting plates comprise:
    a diffusing part, one end of which is connected to the illuminated surface, the diffusing part having a width that increases in a direction extending from the illuminated surface; and
    a converging part, one end of which is connected to the diffusing part, the converging part having a width that decreases in the direction extending from the illuminated surface.

3. The docking apparatus of claim 1, wherein the reflecting plates comprise:
    a lower reflecting plate disposed below the germicidal lamp and having a surface parallel to an upper surface of the plate; and
    side reflecting plates connected to both ends of the lower reflecting plate, the side reflecting plates being inclined upward relative to the lower reflecting plate.

4. The docking apparatus of claim 2, wherein the reflection module further comprises a blocking plate configured to cover an upper portion of the diffusing part.

5. The docking apparatus of claim 1, wherein the sterilization unit is disposed below an upper end of the plate, and emits the germicidal light in an upward direction.

6. The docking apparatus of claim 3, wherein a width of the side reflecting plates increases in a direction extending from the illuminated surface for a predetermined distance, and then is reduced.

7. The docking apparatus of claim 3, wherein a width of the lower reflecting plate increases in a direction extending from the illuminated surface for a first distance, and then is reduced.

8. The docking apparatus of claim 3, wherein the side reflecting plates comprise:
    a rear reflecting plate facing the illuminated surface and connected to one end of the lower reflecting plate; and
    a left reflecting plate and a right reflecting plate facing each other and connected to the lower reflecting plate and the rear reflecting plate.

9. The docking apparatus of claim 8, wherein an angle formed between the left reflecting plate and the right reflecting plate is an acute angle.

10. The docking apparatus of claim 4, wherein the blocking plate is disposed on an upper portion of the germicidal lamp and is configured to block the germicidal light.

11. The docking apparatus of claim 4, wherein the blocking plate is spaced apart from the reflecting plates and overlaps with the diffusing part.

12. The docking apparatus of claim 4, wherein the converging part overlaps with a floor cloth, while the diffusing part does not overlap with the floor cloth.

13. The docking apparatus of claim 12, wherein the floor cloth is circular and a length of the converging part is equal to or greater than a radius of the floor cloth.

14. The docking apparatus of claim 3, wherein the germicidal lamp is configured to project the germicidal light obliquely onto the lower reflecting plate.

15. The docking apparatus of claim 1, wherein the germicidal lamp is configured to emit UVC rays.

16. The docking apparatus of claim 2, wherein a length of the converging part is greater than a length of the diffusing part.

* * * * *